(12) United States Patent
Russo et al.

(10) Patent No.: US 7,737,130 B2
(45) Date of Patent: Jun. 15, 2010

(54) PHARMACEUTICAL COMPOSITIONS FOR TOPICAL USE IN TREATMENT OF SKIN OR MUCOUS INJURIES

(75) Inventors: Elisa Mannochio de Souza Russo, São Paulo (BR); Valter Freire Torres Russo, São Paulo (BR)

(73) Assignee: Cristalia Produtos Quimicos Farmaceuticos Ltda., Sao Paulo (BR)

( * ) Notice: Subject to any disclaimer, the term of this patent is extended or adjusted under 35 U.S.C. 154(b) by 0 days.

(21) Appl. No.: 10/471,623

(22) PCT Filed: Mar. 12, 2002

(86) PCT No.: PCT/BR02/00037

§ 371 (c)(1),
(2), (4) Date: Sep. 12, 2003

(87) PCT Pub. No.: WO02/083086

PCT Pub. Date: Oct. 24, 2002

(65) Prior Publication Data

US 2004/0087544 A1    May 6, 2004

(30) Foreign Application Priority Data

Apr. 17, 2001 (BR) .................. 0101486

(51) Int. Cl.
*A61K 31/727* (2006.01)
(52) U.S. Cl. ........................................ 514/56
(58) Field of Classification Search ........... 514/57, 514/56, 218, 423, 54; 424/484, 488; 536/23.5, 536/23.1, 21, 54, 55; 544/350; 530/350; 435/320.1
See application file for complete search history.

(56) References Cited

U.S. PATENT DOCUMENTS

| | | | | |
|---|---|---|---|---|
| 4,837,019 A | * | 6/1989 | Georgalas et al. | 424/59 |
| 5,037,810 A | * | 8/1991 | Saliba, Jr. | 514/56 |
| 5,278,451 A | * | 1/1994 | Adachi et al. | 257/790 |
| 5,378,451 A | * | 1/1995 | Gorman et al. | 424/47 |
| 5,681,849 A | * | 10/1997 | Richter et al. | 514/481 |
| 6,255,295 B1 | | 7/2001 | Henderson et al. | |
| 6,271,213 B1 | | 8/2001 | Henderson et al. | |

FOREIGN PATENT DOCUMENTS

| | | | |
|---|---|---|---|
| EP | 497 162 | * | 8/1992 |
| WO | WO8905646 A1 | * | 6/1989 |
| WO | WO 9851273 A1 | * | 11/1998 |

OTHER PUBLICATIONS

BASF product listing for "cremophor."*

* cited by examiner

*Primary Examiner*—Shaojia Anna Jiang
*Assistant Examiner*—Layla Bland
(74) *Attorney, Agent, or Firm*—Birch, Stewart, Kolasch & Birch, LLP

(57) ABSTRACT

The present invention describes new pharmaceutical compositions in treatment of skin and/or mucous injuries, new therapeutic use of compounds and use of compositions and compounds in treatment of injuries that involve skin and/or mucous, and/or therapies where regeneration or modelling of tissues growth is necessary. Particularly these pharmaceutical compositions are indicated for treatment of injuries caused by burns.

2 Claims, No Drawings

PHARMACEUTICAL COMPOSITIONS FOR TOPICAL USE IN TREATMENT OF SKIN OR MUCOUS INJURIES

This application is the national phase under 35 U.S.C. 371 of PCT International Application No. PCT/BR02/00037 which has an International filing date of Mar. 12, 2002, which designated the United States of America.

The present invention describes new pharmaceutical compositions in skin and/or mucous membrane injuries treatment, new therapeutic use of compounds and use of compositions and compounds in injuries treatment that involves skin and/or mucous membranes, and/or in therapies where regeneration or modeling of tissue growth is necessary. More specifically, the present invention relates to injuries caused, induced or resulting from burns, where quick recovery of tissues involved is desired.

The skin consists in the widest organ existing in the human body. Among the functionalized structures present therein, the vascular system, lymphatic system, glands and nervi, are detached. Interaction of all its structures in an orderly manner, confers to the skin a fundamental role on existence and survival of the livings, constituting an efficient interface between external ambient and internal organs, which main function is to protect from water loss, contingent intruders, strange material, pathogenic organisms and microorganisms. Further to these functions, skin is able to eliminate a series of catabolites originating from internal biochemical processes and to maintain the ideal temperature constant for the adequate functioning of living organisms.

Since it is an organ which basic function is the protection, its integrity is of utmost importance and any decharacterization of such wide organ, either by rupture or any other medium that presents contingent risk, shall be followed by a mechanism that promotes its immediate recovery.

Skin is structurally composed of two tissue layers, completely different from each other and bonded to each other throughout its extension. Epidermis is the most external layer, also designated cornea stratum. It is constituted of a series of epithelium stratified cell layers, which quantity of keratin protein proportionally increases on most external layers. This special arrangement makes the most external layers more compact, offering greater protection in relation to excessive water loss, action of strange substances and organisms, besides offering greater resistance to abrasion and injuries. This layer does not contain any blood vessel and is sustained by fluids of the layer immediately beneath the dermis, this one presenting irregular connection arrangements, presenting more complex tissues and containing blood vessels between a series of specialized structures.

Nervis present in this organ, allow identification of various external stimulation as cold, heat, pain and pressure, enabling men to adjust themselves to the environment, in adequate manner, and also to protect themselves before situations that can place their integrity under risk.

Skin integrity can eventually be ruptured, causing a series of problems with reference to maintenance of the internal functions of the organism. This rupture can occur due to perforations, accidental or programmed cuts (surgeries), burns, injuries resulting from degenerating processes, having diseases, congenital anomalies or alterations of biochemical processes as a cause, resulting in ulceration, among others.

Under normal conditions, the body has mechanisms to repair and eventually recover, partial or totally, several skin ruptures, in order to restore its integrity and functionality. This repair process is directly related with rupture extension, tissues affected, injury and patient physical condition. Contamination of exposed tissue by strange substances and live organisms will be another factor that will influence on the mechanism and the velocity of the repair process.

Skin healing process involves particular groups of cells and proteins in a complex biochemical mechanism. This renovation process is generally divided in three temporary phases known as inflammation, proliferation and remodeling.

At the initial stage of inflammation, the platelets present out of the circulatory system become more active, producing aggregation. Thus, they signalize the beginning of the repair process, forming a set of temporary cells to avoid hemorrhage and prevent bacterial invasion. Blood vessels under growth, infiltrates in the affected site, discharging various mediator molecules, including other platelets resulting from growth factors, Willibrand factor, thrombospondine, fibronectine, fibrinogen, 5-hydroxytriptophan, thromboxane-A2 and adenosine diphosphate (Kirsner e Eaglstein, J. Dermatol. 151:629-640, 1993). The set of cells that characterizes the clotting are bonded and provides a matrix of monocytes, fibroblasts and keratinocytes. Chemostatic molecules attract the monocytes that are transformed into macrophages and secreting additional growth factors (Nathan e Sporn, J. Cell Biol. 113:981-986, 1991). Neutrophyls can assist these processes secreting degrading enzymes, the elastases and collagenases, increasing the passage through the basis of cellular membrane. The most important role of the neutrophyls seems to be cleaning the affected tissue or defend the area from contingent intruders, accelerating the process as a whole, removing the dead cells and platelets. Infiltration of neutrophyls ceases within 48 hours approximately, provided that no bacterial contamination occurs. The neutrophyls excess is phagocyted by macrophages resulting from monocytes of the circulatory system. It is believed that the macrophages are essential for an efficient recovery process, also being responsible for the phagocytes process of pathogenic organisms and for the cleaning of other materials strange to the body. Moreover, they deliver innumerous factors involved in subsequent events in tissue recovery process.

The second recovery stage, the proliferation, generally begins 48 hours after occurring tissue injury. Fibroblasts begin to proliferate and migrate to the interior of affected space, starting from the already bond tissues and reaching the end of injury. Fibroblasts yield collagen and glycosaminoglycans, stimulating a proliferation of endothelial cells. Endothelial cells will promote the growth of a new net of blood vessels. Collagenases and plasminogen activators are secreted from keratinocytes. If the recovery process is not disturbed, occurring the adequate supply of nutrients with oxygen, the keratinocytes will migrate to the affected tissue. It is believed that keratinocytes only migrate on live tissues and, as a consequence, keratinocytes migrate through areas beneath dead tissues and in interface between the affected area and that already recovered. Afterwards, the affected area suffers twitch. Angiogenese, formation of new blood vessels in response to chemotatics signals (Folkman and Klagsbrun, Science 235:442-447, 1987), and fibroplasias, accumulation of fibroblasts and formation of tissues granulation, also occur during the proliferating phase.

The third and last recovery stage, the remodeling, starts when the epithelium is already recovered. In this phase, which can be extended for many years, the affected tissue obtains its normal strength, slowly undergoing structural readjustments, always on account of depth, as well as the extension of the affected area. Remodeling of tissues is followed by the secretion of cellular matrix components, including fibronectine, collagen and proteoglycan, which serve as a support for the cellular migration and for the tissue. The type III collagen, synthesized at the initial stages of the recovery process, is substituted by type I collagen, the most permanent form, by a response proteolitic process. The affected surface is subsequently coated with an enlargement process, making the surface smoother. These epithelial cells are spread at layers underneath the unstructured area, in order that the affected layers and those above it are slowly substituted or recovered.

This complex process of natural regeneration absorbs considerable time and can be affected by pathological conditions as infections, maceration, dry skin, patient overall health, want of nutrition and others that can lead to chronic ulcer formation, making this process still slower. Other severe conditions can be established in tissues regeneration course. Ischemia, for example, refers to a pathological condition resulting from a located dysfunction of the vascular system, resulting in inadequate blood supply with subsequent damage to the affected cellular tissue. In such cases, re-vascularization, by angiogenese stimulation or by surgery, shall precede the normal course in the recovery process of damaged tissues.

A specific case of skin integrity rupture is related to burn traumas. Burns represent one of the most painful processes that can be established in this tissue, needing the establishment of a coordinated therapy to help its recovery and pain treatment.

Burns can be caused by several factors, among which, exposure to high or low temperatures, exposure to chemical compounds, by electricity, by exposure to radiation and mechanical friction. Burn severity and its risk are evaluated according to the amount of affected tissue and depth reached. The amount of affected tissue is represented by the percentage of burned corporeal surface (BCS). In this type of evaluation, burns can be divided into small, moderate, large or massive burns, where regions inferior to 15% of BCS, from 15% up to 49% of BCS, from 50% up to 69% of BCS and over 70% of BCS, respectively. The extension of the affected area is determined through Lund-Browder scheme, which takes into consideration the burn proportion, in accordance with the age of the burned patient. Another rule that is most used for determining the extension of the affected area is that known as Wallace Rule or Rule of Nines, a technique less efficient than the foregoing, however, easy to memorize, being very much employed in emergency cases. This rule applies a value equaling nine or nine multiple to the affected parts, being 9% for each superior member, 9% for the head, 18% for each inferior member, 18% for each torso face and 1% for the genitalia.

The classification as first, second and third degree corresponds to burn depth. The first-degree injury corresponds to the burn that affects the skin most external layer (epidermis), not producing hemodynamic alterations, however the affected region is found hyperemic in absence of blisters or phlyctenae. This type of injury can be observed in erythemae resulting from sunrays or heated water. The second-degree injury affects either the epidermis as part of the dermis and is mainly characterized by the formation of blisters or phlyctenae, as those resulting from scalding or thermal injury resulting from overheated liquid. The third-degree injury endangers the totality of skin layers (epidermis and dermis) and, in many cases, can affect other tissues, as the subcutaneous cellular tissue, muscular tissue and bone tissue.

Third-degree burns are considered as the most severe of all thermal injuries, producing deforming injuries. For being deeper, it eliminates the nerve endings responsible for shooting the painful message. These types of burns need transplanting for recomposing destroyed tissues, since the structures and organelles necessary for the natural recovery process, were eliminated.

Since burns are wounds that involve the skin, they develop afore mentioned complex process of regeneration and recomposition of injured tissue. The speed or grade of re-epithelization of the affected region is so small as the greater the area involved is, considerably increasing the recovery time, when the injuries start to cover a body surface over 10% or 15%.

Immediately after the burn trauma, the inflammatory chase is developed wherein various agents are delivered, occurring deposition of fibrins and platelets activated on the wound surface. A matrix rich in organic material is yielded, able to enclosure bacteria and other strange substances, which frequently aggravates the case, due to sepsis that can follow trauma.

During this inflammatory process a great quantity of exudates crop out of the burned region, leading the patient to an intense loss of liquids, which, depending on the burn extension and depth, can cause a severe dehydration case. The intense inflammatory process extends to adjacent tissues, factor that endangers the functions of these tissues initially intact.

The anoxic environment of burn wounds is extremely hostile, presenting an acid pH, with high lactate levels and low glucose levels, resulting from low or nearly inexistent oxygenation level of tissues, provided by the vascular system endangerment and actuation of phagocytes and bacteria.

Tissues under formation, as a consequence of these factors, cannot receive adequate nutrients supply and suffer necrosis. Tissues with necrosis must be removed in order that the regeneration process can be resumed in the endangered region. Removal of these tissues is surgical and made under anesthesia. Despite this surgical procedure it does not represent further sufferance for the patient, his recovery is endangered, since a new tissue will be formed in substitution to the one removed, extending the internment time and increasing the possibility of area contamination by microorganisms.

Extensive and deep burns cause alterations that are extended far beyond the affected local. Associated therewith are anatomic, metabolic, physiological, endocrinology and immune alterations, requiring special care. Significant fluid losses, delivery of inflammatory multi-mediators and contamination by bacteria, occur. When disseminated in central organs through circulation, bacteria and inflammatory mediators can cause cardiac endangerment, failure of gastrointestinal mucous integrity and in extreme cases, multi-organic failure. Endangerment of aerial ducts tends to aggravate and accelerate such responses.

Hemodynamic alterations that occur after severe thermal injuries include decrease of cardiac output and reduced volume of circulating plasma, contributing all to a hypovolemic shock. Inflammatory mediators (including cytokines, prostaglandin, nitric oxide and superoxide ions) have been implied in causing further damage to tissues. It is believed that despite local benefit, such mediators induce undesirable effects when reaching significantly high levels. As an example, a greater damage to tissues can be caused by delivery of proteolitic enzymes and superoxide ions of macrophages and activated leucocytes.

In view of these information, it can be observed that burns are situations that develop unbalance in a series of natural organic mechanisms, not limited to endangered tissues only, but indeed involving innumerous organs that can be affected with alterations resulting from trauma. Additionally, large thermal injuries induce to a sharp increase in basal metabolic rate. In the phase immediately after burn, energetic needs of burned patient get close to the limit of physiologic reserves, exceeding up to twice the basal caloric levels required by a healthy person (Cunhingham and col in "Measured and predicted calorie requirements of adults during recovery from severe burn trauma", Am. J. Clin. Nutr. 49:404-408 (1989); Saffle and col. in "Use of indirect calorimetry in the nutritional management of burned patients"—J. Trauma 25:32-39 (1985)). The case of hyper metabolism has intensity and variable duration depending on the patient, the extension and depth of BCS, the presence de infections and efficiency of the initial treatment (Wolfe in "Relation of metabolic studies to clinical nutrition—the example of burn injury" Am. J. Clin. Nutr. 64:800-808 (1996)). In these cases a protein-caloric want of nutrition can be installed, which can be evidenced by great losses of corporeal weight and nitrogen balance remarkably negative, usual consequences of the metabolic response to burn (Goodwin in "Parenteral nutrition in thermal injuries" Clinical Nutrition: Parenteral Nutrition—Rombeau, J. L. ed, W. B. Saunders Company, Philadelphia, p. 566-584 (1993); Gottschlich and cols. in "Enteral nutrition in patients with burn or trauma" Clinical Nutrition: Enteral tube feeding—Rombeau, J. L. & Caldwell, M. D. eds, W. B. Saunders Company, Philadelphia, p. 306-324 (1990)).

Great nitrogen corporeal losses, observed in burned patients, mainly occur due to protein exudation through burned skin and also by the fact that, under such catabolic stress situation, corporeal proteins can become the metabolic substrate used for production of 15 to 20% of total energy required by the organism.

Further to these abnormalities, it can be observed that burned patients present increase on levels of cathecolamines, cortisol and glucagons, in the presence of normal or slightly increased levels of insulin (Wolfe in "Relation of metabolic studies to clinical nutrition—the example of burn injury" Am. J. Clin. Nutr. 64:800-808 (1996); Wilmore in "Hormonal responses and their effect on metabolism", Surg. Clin. North Am. 56:999-1018 (1976)). These hormonal alterations promote increase of proteolysis and lipolysis with delivery of great quantities of amino acids, specially alanine and glutamine (Cynober em "Amino acid metabolism in thermal burns", J. Parent. Enteral Nutr. 13:196-205 (1989)), glycerol and free fatty acids in systemic circulation. Provided that burned patients present glucagons increases proportionally higher than insulin, free fatty acids metabolism for keto groups will be impaired and glycerol and amino acids will be used for production of glucose by glyconeogenetic via.

Apparently, glucose is the preferential energetic substrate of leucocytes, macrophages and fibroblasts of burned area (Wilmore and cols. in "Influence of the burn wound on local and systemic responses to injury", Ann. Surg. 186:444-458 (1977)). Free fatty acids are used as alternative energetic source by non-burned skin and by muscular tissue, or are metabolized in cyclo-oxygenasis duct, with production of eicosanoid pro-inflammatory compounds (Grimble in "Interaction between nutrients, pro-inflammatory cytokines and inflammation", Clin. Sci. 91:121-130 (1996); Hwang em "Essential fatty acids and immune response", FASEB J 3:2052-2061 (1989)). Prostaglandins, prostacylins and thromboxane of series 2, resulting from metabolism of linoleic acid derivatives, have a significant role in systemic inflammatory response post-burn.

This complex unbalance picture will be presented as much severe as the time involved in recovery of injured tissues is greater. The quick skin recovery of burned individuals is of utmost importance for recovery of his normal organic functions.

Treatment of burned individuals will involve several factors and procedures starting from an accurate diagnosis of trauma depth and extension. During the treatment other aspects will still be evaluated, as the age, physical and mental state of the patient, his schooling, social integration, as well as his living condition and his occupational capacity.

First aid measures rendered to victims help in restraint of affected region (natural expansion of the wound results from proteins degenerating process that is developed), providing the initial cleaning of the region and removal of residues from tissues, clothes, solvents and other materials that can be found present in the wound.

Subsequent recovery process of affected tissue will be a much wider process and, depending on the burn degree and its extension, will take some days up to many months for recovery. Among the phases involved, proliferating phase is the most delicate, which needs for particular and effective treatments will be intense, due to its importance in formation of the new tissue that will regenerate or substitute the endangered or lost tissue.

The proliferating phase that follows the inflammatory phase, as afore mentioned, consists in a process that will involve production of glycosaminoglycan by cells that will proliferate and migrate to traumatized tissue. These glycosaminoglycan will stimulate proliferation of endothelial cells, able to promote growth of a new vascular net, a basic and essential for tissue regenerating process.

Glycosaminoglycans are mixtures of proteoglycans, which are composed of repeated disaccharide units, where D-glycosamine ou a D-galactosamine are always present. Generally, glycosaminoglycans contain uronic acid and sulfate groups chemically linked by ester or amide linkages. Six distinct classes are generally recognized: hyaluronic acid, chondroitin sulfate, dermatan sulfate, heparin sulfate, keratan sulfate and heparin.

Heparin is a dextrorotary glycosaminoglycan, consisting in a mixture of various polysacharidic chains, composed of repeated D-glucosamine units and also L-idurenic acid or D-glucuronic acid. Its molecular weight ranges between 6.000 Daltons to 30.000 Daltons, which will depend on either the obtainment source or the methodology, employed for its isolation.

Particular classes of heparins are known as low molecular weight heparins that which correspond to heparins in which obtainment process are promoted depolymerization of natural heparin, obtaining less functionalized fragments. Molecular weight of these heparins ranges between 3.000 Daltons to 8.000 Daltons.

Heparin sulfates refer to glycosaminoglycans that contain a repeated disacharidic unit similar to that of heparin, presenting, however, more N-acetyl groups, less N-sulfate groups and lower degree of O-sulfate groups.

Generally, concentrations of glycosaminoglycans are expressed in international Units (IU). This International Unit refers to the anti-clotting activity observed with these glycosaminoglycan determined "in vitro" by comparison of the ability in certain conditions to prolong the clotting factor of an ewe plasma recalcified-citrate with the same ability of a reference preparation of calibrated heparin in International Units. The international unit is the activity contained in a certain quantity of International Standard, which consists in a quantity of pig mucous heparin lyophilized. The World Health Organization determines the equivalence in International Units of International Standard.

The ability in prolonging the blood clotting time is the most known heparin property. Further to the anti-clotting activity, it also shows enzymatic antiproteolitic activity antithrombin, platelet antilyse, thrombolitic, antiserotonergic, and antihistaminic.

There are several references in literature that deal with administration of different drugs in skin injuries and burns treatment, as well as the development of devices, bandages, solutions, creams, waxes and gels for been employed on traumatized regions.

Among these references, there is the U.S. Pat. No. 4,732,755 (Grana) that promotes the application of powder sodium polyacrylate covering the burned region such substance is later wetted by spraying sterilized distilled water. The paste formed dries on its outer portion forming a surface similar to parchment. This injury coating material can stay on the local between two or three weeks, in order to minimize water loss, avoiding capillary permeability and preventing infection of the burned area. The removal of this material from the injured surface is made by dislodgement, which the author state being simple and easy since the skin is regenerated. A problem associated to this type of treatment is the unavailability of administering other substances on the treated surface as, for example, antibiotics that need to be administered for controlling bacterial infection usual in such type of injury.

The U.S. Pat. No. 4,837,019 (Georgalas et al) proposes burns treatment with a composition based on polyglyceryl-methacrylate, glycerin, allantoin, panthenol, aminoacid complex and fibronectin. According to the author, this composition presents the property of reducing the tissue loss of humidity, necessary for its normal recovery. This patent does not approach the use of glycosaminoglycan in burns treatment.

The U.S. Pat. No. 5,009,890 (DiPippo) describes a product for skin burn treatment, as a hydrogel (water soluble), biodegraded, where the active ingredients are water and a mixture extracted from the tea tree. A gum is used for maintaining water and tea under gel state, further to other substances that can be added in order to prolong the validity term of such composition. Tea originates in a particular tree, existing in Australia, which presents terpenes, terpinol between several other compounds, which the author states existing in enantiomeric form that is adequate for presenting antibacterial action besides promoting tissues recovery. Formulates containing mainly natural products with restricted characteristics, as the case seems to be, usually present great activity variation from one lot to the other, since the components extracted can greatly vary from crop to crop, relatively altering the activity presented in end-product.

The U.S. Pat. No. 5,616,619 (Stofer) describes the administration of a combination containing lemon juice and a salt, formulated as a pasty composition for burns treatment. Among pharmaceutically acceptable salts, preferably is sodium chloride, presenting or not small quantities of potassium chloride and potassium iodide, being the ideal composition usually found in common salt. This pasty composition must be employed on burned region, and maintained in this region by means of bandages. There is no reference to possible deleterious effects that the lemon astringency can cause to traumatized region, neither descriptions relating to pain caused by the method of application. Another important factor is the fact that the composition must be stored in refrigerator, an evidence of its short stability.

The U.S. Pat. No. 5,653,994 (Schneider, et al.) deals with methods and compositions for burns treatment, allergies, traumas or diseases of the dermis, epidermis, mucous membranes and subcutaneous tissue, particularly traumas resulting from burns. The method includes application of an aqueous solution of hydrogen peroxide and some aluminum salts of carboxylic acids to the trauma, guaranteeing enough contact time of the solution with the skin affected area, accelerating process for its recovery. The ideally desired contact is reached when bandages wetted with the solution are applied on the affected region, and maintenance of the bandage humidity up to treatment ending. This humidity maintenance is reached with bandages coating with plastic film, which inhibits humidity evaporation. The need for changing the bandages, in order that the same remain humid and do not adhere to the affected region, confers a disadvantage due to the pain involved in this procedure.

The U.S. Pat. No. 5,834,008 (Greenspan et al) describes a method for injuries treatment involving the injury contact with an effective quantity of a bioactive glass and a topic antibiotic, and a composition to accelerate the recovery of injuries and burns that include particles of bioactive glass and at least a topic antibiotic. The so-called bioactive glass consists in a particular composition of silicon oxide, calcium oxide, sodium oxide and preferably phosphorus pentoxide, in determined quantities, which particles have the adequate size. The author suggests that, due to the great superficial area and its reactivity, the particulate bioactive glass provides deliver of sodium increasing the pH and oxygen in the injury or burn, that usually present acid pH. This provides a bacteriostatic effect allowing the antibiotic to activate various growth factors implied in the repair of damaged tissues. The author makes a remark on the utilization of the composition, emphasizing that the antibiotic and particulate bioactive glass must be previously admixed to the use, since this bioactive material reacts with the antibiotic promoting its inactivation. This represents na obstacle in the utilization of this type of composition, since skin infections are frequent and the adequate use of topic antibiotics would be endangered due to its quick inactivation by the bioactive material.

The U.S. Pat. No. 6,099,866 (Slimak) describes the utilization of beeswax and oil, with or without water addition, and the utilization of such compositions for treating animal skins, including men on first, second and third degree burns, caused by various sources as, flames, hot liquids, chemical agents, cold and electric among others. These compositions can be used also in the prevention of burns, besides presenting activity to accelerate the recovery of various other types of skin injuries. Further to these properties, the author states that these compositions can protect tissues, forming an efficient barrier against irritating agents that can come into contact with the injured region. In order to be adequate for the specified use, wax must undergo a very hard and particular extractive process in order to only collect what the author calls "virgin wax". This wax can be used in various presentations as creams, ointments, oils, and lotions among others. The composition is applied on the affected region and massaged in a prolonged form to promote its absorption by the remaining tissues, a procedure that can represent a hard trauma to the patient due to the pain developed.

The U.S. Pat. No. 5,650,495 (Michio e Kazuyuki) reveals that one protein isolated from certain rat tissues present the property of controlling growth of neural cells, altering the action of one of the growth factors, heparin-linked, named osteoblast-specific-factor-1 (from the English OSF-1). The object of this invention is to provide a new protein and useful as drug for neural dysfunctions treatment, as well as in osteogenetic diseases.

The U.S. Pat. No. 4,837,024 (Michaeli) proposes a composition of suspension of collagen fibrils, with a minimum quantity of glycosaminoglycan, between 2.8 and 3.8%, covalently unlinked, supported by a group of bandages, tissues, gauze or strips for utilization in treatment for recomposition of epithelial tissues. It deals with a solid suspension that must be used powdered or wet. The author states further that the proportion between collagen and glycosaminoglycan must remain within a quite narrow range. In event of unbalance, existing a greater quantity of collagen for example, cellular migration will be endangered. If, on the other hand, there exists presence of a greater quantity of glycosaminoglycan, can occur hemorrhage or inflammation and if its concentration is very low, it will reduce cellular migration. The author alerts that these compositions must be maintained under refrigeration, in order to avoid growth of microorganisms and that must not be frozen so that no interference in the suspension occurs. These characteristics evidence the small stability of such suspensions. The narrow and restricted concentration range between the two formulation components is another unfavorable factor, since injured tissues tend to have differentiated absorption characteristics. As the active principles are in solid state, its absorption will certainly be made under different speeds, possible to occur local concentrations inappropriate for an ideal therapeutic activity of such compositions.

The U.S. Pat. No. 5,703,047 (Wilson, S. E.) presents a method for treatment of dry-eye-syndrome or dry keratinous conjunctivitis, likewise dysfunctions in the cornea caused by accidents, surgical procedures that affect the cornea and disorders from several sources, which alter the normal endothelium and epithelium recovery process. The authors also present a method for maintaining the vitality of the cornea extracted, so that the transplant presents a greater success possibility. The invention relates the use and the controlled delivery to growth factors of particular hepatocytes and keratinocytes in vivo and in vitro, thus stimulating proliferation and mobility of cornea cells in an adequate manner. The authors also present the utilization of such growth factors for the treatment of epithelial recomposition after surgical procedures of cornea transplants. Useful compositions include growth factors that are yielded in the epithelial and endothelial cornea extract and lachrymal cells. In this patent the utilization of glycosaminoglycan is not made and even the treatment suggested is not tested in other organs or tissues, besides the cornea.

The U.S. Pat. No. 5,902,799 (Howard, H. et al) presents a method to promote the controlled angiogenese on tissues of mammals by the local application of a composition of fibroblast and epidermal growth factors with derivatives of cyclodextrin polyanionic in a medium physiologically compatible. The method has application in treatments of skin recomposition caused by ulceration, administered via hypodermic injection and in bone reconstitution in mammals, by local administration directly on the surface of bone tissue. In this patent the use of glycosaminoglycan in reconstitution of tissues is not approached also.

In U.S. Pat. No. 5,958,379 (Juergen et al) the authors suggests a pharmaceutical carrier for the use of innumerous active substances. This pharmaceutical carrier corresponds to a liposome composition, in which various active principles can be adequately aggregated in concentrations normally superior to the carriers usually used. Between the substances mentioned are heparin e heparinoid in general, which can be aggregated in the liposome vesicles, in concentrations much superior to the usual presentations, so that the injecting via can be substituted by the topic via for treatment post-surgeries for thromboembolics prophylaxis or for prophylaxis of thromboembolics infections, for the therapy of arterial and/or venous thrombosis, of embolisms, cardiac attacks and unstable pectoris angina, for inhibiting coagulation during the treatment or during surgeries with extra-corporeal circulation and for the treatment of coagulation disturbances consequential from an increase in thrombocytes, as well as from factors of plasmatic coagulation. The treatment with the compositions containing heparin is solely restricted to these applications, existing no mention to its properties when used in skin injuries treatment, specially burns.

The U.S. Pat. No. 5,037,810 (Saliba) describes the use of heparin in transplants, which must be employed in removal, transport and surgical procedures for implanting in the receiving organism. According to the author, heparin can be still employed as a preserving agent of tissues in judiciary medicine. The author describes also the application of heparin and similar compounds with substances useful in skin injuries treatment such as circumcisions, injuries by freezing, dermatitis, fissures, fistulas, ulcerations, decubital ulcers, psoriasis, insect and snake bites, among other types. Some modalities of treatment in transplant cases and also for use for skin recovery in some type of injuries are suggested. Heparin is used by injection and also topic via. The author argues that solutions pH must be acid, around 5.5 in order to present effect. In this patent no pharmaceutical formulation or composition containing heparin is described, not even argued or suggested compositions or adequate doses for skin injury treatment caused by burns, being a patent that describes a therapeutic procedure for the several treatments proposed.

The U.S. Pat. No. 4,760,131 (Sundsmo) describes compositions containing collagen, heparin and what the author calls non-degranulated platelets, which are prepared mixing an anti-clotting agent to the blood and separating the platelets later, by centrifuging. The compositions are maintained under low temperature, between 2 and 6 Celsius degree, evidencing the low stability. Preparation of platelets used in the composition is quite delicate and complex, involving expensive technology, economically hindering the production of these compositions in industrial quantities.

In view of the differences mentioned it is possible to verify the great variety of treatments and compositions proposed for the recovery of injured skin tissues. However, up to now, no composition exists in the market that shows real efficiency in burns treatment.

Treatment of injured individuals caused by burns, mainly extensive and/or deep, still represents an extremely lacking field, where new therapies, compositions and medicaments that enable an accelerated recovery of endangered tissues can help and improve the quality of the treatment offered, enabling a quick and less traumatic recovery for patients.

Some references previously mentioned introduce the use of glycosaminoglycan in skin injury treatment. However, these substances have been used only as accessories in treatment of several types of injuries, usually combined with innumerous other active substances to reach some type of effect. The combination of several active substances as glycosaminoglycan provides a deleterious effect in the activities that it can present in recovery of tissues as those of skin. The low efficiency observed in skin injury treatment with glycosaminoglycan, specially the most extensive caused by burns seem to be related with endangerment of the orienting power in directing new tissues growth, resulting from physical interference of the other formulation components, which hinders this action. Possible chemical inactivation of the functions present in such type of substances are not discarded, which are essential in growth orientation and modeling of skin tissues in a regeneration process.

Among the mentioned references, some use heparin or heparinoid for the treatment of several dysfunctions. The reference that dealing with liposomes does not approach the application of heparin to help in the regeneration of skin tissues, searching a topic composition that can substitute the injecting administration via of heparin for treatments of several thromboembolics disturbances. Two other references use collagen and heparin in solid or semi-solid compositions, and the other one as a special aggregate of platelets, which obtainment involves economically unfeasible technology. It can be observed that both present stability problems and very narrow ranges in the proportions of its components with effective therapeutic power. Burn injuries are usually extensive and non-homogeneous, presenting quantitative and qualitative differences with reference to discharged fluids and remaining tissues, which factor could easily provoke located unbalances in the proportions of its constituents. These unbalances would be intensified in solid or semi-solid compositions, to which careful bathing can be added, for removal of the material remaining from previous administration, at each new application of the composition, making the treatment of burn injured individuals much painful and traumatic.

One of the objectives of the present invention is to present new pharmaceutical compositions containing glycosaminoglycan, preferably heparin, low molecular weight heparin, heparin sulfates and heparinoid in general, as well as its acceptable pharmaceutical salts, for the topic treatment of skin injuries, more specifically injuries resulting from burns.

We found out that the use of compositions of this invention presents a remarkable activity in recovery of skin endangered by injuries, specially burns, including extensive and/or deep burns.

Studies are being address aiming at clarifying the real mechanism through which such substances actuate in growth or regeneration of tissues, particularly the skin. The preliminary results point to the possibility that the regenerating process of these tissues results from the orienting power of these substances in promoting the growth of the vessels that will supply the new tissues, or also in chemically orient the migration of fibroblasts and other cells involved in the growth of tissues in parallel with the vessels under formation, optimizing the regenerating process. The located anti-clotting power of these substances on topic application also seems to contribute, avoiding interruption or occlusion of recently formed micro-vessels and enabling a minimum necessary blood supply to the ends under growth, that is an essential factor for continuance of process.

Another objective of the present invention is to propose the use of pharmaceutical compositions containing glycosaminoglycan, preferably heparin, low molecular weight heparin, heparin sulfates and heparinoid in general, as well as its acceptable pharmaceutical salts, for the topic treatment of skin injuries, more specifically injuries resulting from burns.

Up to now, compositions described for the treatment of skin injuries, specially the compositions containing glycosaminoglycan for the treatment of burns have shown to be inefficient in exercising a growth modulating effect and regeneration of skin tissues.

This invention relates with topic pharmaceutical compositions containing glycosaminoglycan, more preferably heparin, low molecular weight heparin, heparin sulfates and heparinoid in general, and/or its acceptable pharmaceutical salts, employed in concentrations ranging from 0.01 mg/mL to 10,000 mg/mL, more preferably in concentrations from 0.1 mg/mL to 5,000 mg/mL. Other components present in these compositions are the osmolarity-correcting agents, among it preferably sodium chloride, employed in a concentration of 0.001% to 5.0% in composition weight, most preferably of 0.01% to 3.0% composition weight; preserving agents, among them preferably paraben, benzylalcohol, chlorobutanol, chlorocresol, cresol, benzethonium chloride, benzalkonium chloride and/or combinations among them, employed in a concentration of 0.0001% to 30% in weight of end-composition, more preferably in a concentration from 0.0001% to 20% in weight of end-composition. Inorganic solvents and/or biologically compatible organic, employed in order to bring these compositions to the adequate end-compositions of glycosaminoglycan, add these compositions. As these solvents are used to average the final concentration of the composition, they are utilized using the denomination q.s.t, which means "quantity sufficient to" fulfill a certain final volume, when approached in the compositions described in the examples of the experimental part.

Additionally these compositions can present other substances with the purpose of reaching specific properties, implementing some of its characteristics. Thus, the compositions of the present invention can additionally present one or more of the following agents:

Wetting agents: among them preferably being employed sorbitol, propyleneglycol, glycerin and/or combinations among these, being used in a concentration of 0.01% to 60% in weight of end-composition, most preferably in a concentration of 0.1 to 50% in weight of end-composition;

Surfactant/surface-active agents: selected from the anionic, cationic surfactants/surface-active and the non-ionic and/or combinations between them, more preferably the non-ionic, employed in a concentration of 0.0001% to 40% in weight of end-composition, and most preferably in a concentration of 0.0001% to 20% in weight of end-composition;

Thickener agents: preferably selected from methylcellulose. hydroxyethylcellulose, hydroxypropylcel lulose, sodium carboxymethylcellulose, xanthan gum, carbomer and/or combinations thereof, between them, being employed in a concentration of 0.01% to 60% in weight of end-composition, more preferably in concentration of 0.1 to 50% in weight of end-composition;

Buffers: Preferably selected from buffers of phosphate, citrate, carbonate, acetate and/or combinations among these, preferably being employed in solution form, in concentration of 0.01 M to 10.0 M in water, more preferably in a concentration of 0.1 M to 10 M, where in end-composition final are added in a concentration of 0.01% to 80% in weight, more preferably in a concentration of 0.1% to 50% in weight of end-composition.

As previously mentioned, glycosaminoglycan are mixtures of proteoglicanas, which are composed of repeated disacharidic units, where a D-glycosamine or a D-galactosamine are present. Six distinct classes of glycosaminoglycan are generally recognized: hyaluronic acid, chondroitin sulfate, dermatan sulfate, heparin sulfate, keratan sulfate and heparin.

Among the glycosaminoglycan preferably used in the present invention heparin is detached, previously mentioned as being a dextrorotary glycosaminoglycan consisting in a mixture of various polysacharidic chains composed of D-alucosamine repeated units and also D-iduronic acid or D-glucuronic acid, which molecular weight generally ranges from 6.000 Daltons to 30.000 Daltons, which will depend either on its source of obtainment or the methodology employed for its isolation. Another glycosaminoglycan preferably used in the present invention deals with a particular class of heparin known as low molecular weight heparin, corresponding to heparin in which obtainment process are promoted de-polymerization of natural heparin, obtaining smaller fragments functionalized with molecular weight generally ranging between 3.000 Daltons to 8.000 Daltons. However, heparin sulfates, another class of glycosaminoglycan preferably used in present compositions, present a repeated disacharidic unit similar to heparin, but presenting more N-acetyl groups, less N-sulfate groups and lower degree of O-sulfate groups. In the present invention these glycosaminoglycan are preferably employed in a concentration of 0.01 mg/mL to 10,000 mg/mL, most preferably in a concentration of 0.1 mg/mL to 5,000 mg/mL.

The ionic and/or saline equilibrium of present compositions must also be carefully observed, since they will be in direct contact with unprotected surfaces and exposed tissues, under constant process of fluids discharging, in which a disequilibrium of ionic and/or saline concentration can cause a painful and uncomfortable process when administering these compositions, besides endangering recovery of tissues. For maintenance of osmotic equilibrium these compositions present an osmolarity-correcting agent, chosen between biologically adequate agents, preferably using sodium chloride. This osmolarity-correcting agent will be employed in concentrations ranging from 0.001% to 5.0% in weight of end-composition, most preferably from 0.01% to 3.0% in weight of end-composition.

Compositions in present invention still can present included preserving or stabilizing agents pharmaceutically acceptable, in order to increase its physical-chemical and microbiological stability. Among the available preservers, preferably used in the present invention are paraben, benzylalcohol, chlorobutanol. chlorocresol, cresol, benzethonium chloride. benzalkonium chloride and/or combinations among them. Concentration of preservers or stabilizers will range in accordance with the chosen agent, being preferably employed in a range from 0.0001% to 30% in weight of end-composition, most preferably in a range from 0.0001% to 20% in weight of end-composition.

In order to confer additional properties to the compositions of the present invention other agents cam be employed, implementing some particular characteristics. Among these agents, the present compositions can contain one or more agents selected from those presenting wetting properties, surfactants also know as surface-active, thickeners and buffering agents.

Wetting agents can be employed in order to avoid exsiccating or dehydration of traumatized regions, resulting from atmospheric air contact with exudates liquids. Among the adequate wetting agents that can be employed in present compositions, preferably used are sorbitol, propylenoglycol, glycerin and/or combinations among these. Preferably used concentration ranges from 0.01% to 60% in weight of end-composition, being most preferably used in a concentration of 0.1% to 50% in weight of end-composition.

Previously it was mentioned that traumatized regions are, in most times, very sensible to touch. Compositions to be administered on traumatized tissues must preferably present a high absorption power, so that the active component can reach the injured tissue, in effective and immediate form, promoting the adequate regenerating power. Surfactant agents, also known as surface-active agents, are substances having the property to reduce the superficial stress of the present compositions when in contact with injuries. Therefore, compositions can be instantly absorbed by the affected tissues, existing no inconvenience for dripping from the affected region in event of liquid presentations. Among adequate surfactants/ surface-active for the compositions of the present invention, anionic, cationic and non-ionic are included. Among these, preferably used can be chosen between non-ionic, as derivatives of alkylethers of polyoxyethylene (for example Steareth, Ceteth), polyoxyethylene derivatives of castor oil (for example Cremophor which is trademark of the polyoxyl-35-castor oil), polyoxyethylene (for example Myrj, Crodet), polyoxyethylene derivatives of sorbitol fatty esters and anhydrides thereof (for example Tween, Spain, Octoxynol), fatty derivatives of glycerides (e.g. Arlacel), copolymers of polyoxyethylene-polyoxypropylene (for example Poloxamer) and/or mixtures between these substances. Concentrations of these surfactants/surface-active can range between 0.0001% and 40% in weight of end-composition, depending on the component employed, most preferably being employed in a concentration of 0.0001% to 20% in weight of end-composition.

Another great importance factor in the present invention refers to the application manner of these compositions. Burns, especially those of first and second degrees, confers an extremely pronounced sensibility to the affected region. Due to sensibility of nervous endings, the affected region usually presents extremely painful and very sensible to touch. Compositions prepared in the form of pastes, waxes, thick cream, ointments or other types, in which application spreading of the composition by hard or prolonged contact is necessary, can cause extreme discomfort to the patient due to the pain associated to administration.

In order to maintain the compositions of the present invention with consistency adequate for administration on sensitive regions, the viscosity of these compositions can be maintained at a desired level by using pharmaceutically acceptable thickener agents. Among thickener agents preferably used in present invention are methylcellulose, hydroxyethylcellulose, hydroxypropylcellulose, sodium carboxyethylcellulose, xanthan gum and/or mixtures between these agents. In the present invention, thickeners are employed in quantities ranging from 0.01% to 60% in weight of end-composition, most preferably in concentration of 0.1 to 50% in weight of end-composition.

In present invention compositions pH must present itself in a range from 4.5 a 8.5, since the compositions with pH inferior to 4.5 and superior to 8.5 can expand the risk of damages to tissues endangered by the trauma or cause itching on the application local, causing discomfort to the patient and expanding his psychological trauma. Usually the formulated compositions already reach the ideal range between 4.5 and 8.5 aforementioned, however, may occur that the same stay slightly over or bellow the ideal. In such cases, pH adjustment is made through the conventional manner, that is, by adding hydrochloric acid or sodium hydroxide for correcting its value.

Maintenance of this pH range can be aided with the use of buffers in the compositions to be prepared. Among the buffers that can be used in the present invention, acetate, citrate, carbonate and/or phosphate are preferably employed. These buffers are preferably used in the form of solution in concentration ranging from 0.01 M to 10.0 M, most preferably in concentration from 0.1 M to 5.0 M, being added to compositions in quantity ranging from 0.01% to 80% in weight of end-composition, most preferably in quantities from 0.1% to 50% in weight of end-composition.

Compositions of the present invention will further present biologically compatible solvents in order to dilute, homogenize or disperse the agents employed. These solvents are selected from pharmaceutically acceptable inorganic and organic solvents, preferably water, acid or alkaline aqueous solutions, ethanol, propanol, isopropanol, ether, and/or combinations between these. Most preferably, water and aqueous solution slightly acid or alkaline are employed.

Compositions presented in the present invention are preferably in the form of aqueous solutions, gels or solutions with capacity to form gels during its application. As a form of application, the compositions prepared in solution forms are preferably sprayed on the wound directly, with no need to spread by contact. Due to its viscous property, gels are presentations which the need for spreading does not require pressure application on the region of administration, also presenting easy spreading property due to its physical form, and appearing as another form of application, also adequate for the treatment of these types of trauma.

Pharmaceutical compositions of the present invention are employed in several treatments in medicine and/or veterinarian fields, more particularly directed to treatments of injured biological tissues, and in promoting accelerated reconstitution, regeneration and/or remodeling of these tissues. In this aspect, skin injuries in general, and mainly burn injuries are included.

Burn injuries present further some other peculiarities that must be carefully studied. Exposure of the tissues usually protected by the skin can be extremely prejudicial to the organism. Endangerment of skin integrity exposes the organism to innumerous harmful agents as the microorganisms, which can easily infect the affected region due to the endangerment of the immune system efficiency. When manufacturing the compositions of the present invention, in order to be employed in topic treatment of these injuries, the low local immune response should be considered, preferably yielding it in sterile form, for not being carriers of contaminants to exposed tissues. For sterilizing these pharmaceutical compositions, can be employed the conventional sterilizing methods that do not interfere with physical-chemical integrity and the activity of its constituents.

Another important aspect of the present invention relates to the application dosage of these compositions. Concentration of the solutions containing glycosaminoglycan, preferably heparin low molecular weight heparin, heparin sulfates and heparinoid in general, as well as its acceptable pharmaceutical salts, shows to be of important relevance in establishment of tissues re-epithelization effects, being particularly useful in the treatment of skin and mucous injuries, including treatment of skin injuries resulting or originating from burns by exposure to high or low temperatures, chemical compounds, several radiation, electricity or mechanics. Studies carried out show that the concentrations or dosages of these substances to be administered, must range from 1,000 IU (International Units) to 50,000 IU for each one percent (1%) of the corporeal surface area of application. As the anti-clotting factors of these substances seem to influence directly on the regenerating power observed in the recovery of skin tissues, also as this activity cannot be disregarded due to the located anti-clotting effect yielded, this type of unity shows to be more adequate in choosing the administration dosage of glycosaminoglycan of the compositions in the present invention.

Additionally, the pharmaceutical compositions of the present invention prepared in the form of solutions, will preferably be available in flasks with spray application device, in order to facilitate the administration. These solutions can present different concentrations, as the appropriate dose can be administered and controlled by the number of times that the spraying device is activated.

The type of applicator for this solution can also vary in accordance with the preference and/or need of the professional in the treatment. In order to reach a percentage of the area of corporeal surface to be recoated with the concentration of the substance employed, the professional can decide by an applicator that promotes the administration of the composition with two or more activations of the spraying device. In general, professionals may use the combination between the different concentrations of these compositions and the different spraying devices, conferring the possibility to reach the adequate topic administration of liquid compositions, through a simple application or through multi-applications on the area of corporeal surface to be treated. This versatility can bring greater facility in drug administration, depending on the extension of the wound, its continuance or not, and the location of the affected region, which can present greater access difficulty, being necessary a more directed or reduced application.

Up to now, treatments of burned surfaces are usually followed by the need for using bandages for application of the administered drugs, being necessary to remove and change these bandages at each new administration. Bathing for cleaning the affected surface are constant and necessary procedures, besides extremely painful. Another frequent procedure is the surgical unrestraint of the affected region aiming at removing the scabs, formations that hinders revascularization and recovery of peripheral circulation in the tissue under formation.

Treatment of burn injuries with the compositions described in the present invention presents innumerous properties favorable to recovery of endangered patients. The regeneration process of the epithelium is considerably accelerated. In some severe cases of second-degree burns, it was observed the full recoating of the injury with fine reepithelized tissue, in approximate periods of 48 to 72 hours. Further to the accelerated recovery of the tissue, can be observed that there is no need of administration of opioid due to absence or little pain manifestation. Generally, the affected region treated with these compositions do not present edematous or presents small edema, factor which can be related to absence or low pain manifestation.

The use of these compositions eliminates the need to use bandages for protection and maintenance of the humidity on the injury local. The need for dairy bathing is not observed, nor the surgical restraint of the injuries, due to non-formation of scabs that hinders the revascularization process of tissues. In some cases were observed formations of fine scabs on the affected region, under which the normality of the revascularization process and integrity of tissues under formation were found.

The quick re-epithelization process of injuries, promoted with the compositions of the present invention, is highly beneficial to reduce sharply the possibility of inflection of the affected region, further to considerably reducing the time necessary for patient internment.

In the following experimental part reported, illustrating examples were presented, but non-exhausting, of possible formulations that can be prepared as described in the present invention and employed for treatment of injuries, specially injuries resulting from burns.

Also reported are some cases where the use of compositions described in the present invention showed its effective properties on recovery of injuries resulting from burns. The results were compared with the recovery records of patients that presented similar injuries and that underwent conventional treatment, presently employed in several specialized medical institutions.

EXAMPLE 1

A pharmaceutical formulation was prepared in the form of a solution containing the following composition:

| SUBSTANCE | QUANTITY |
|---|---|
| Sodium heparin (~150 IU/mg) | 3,333.33 mg |
| Benzylalchool | 9.045 mL |
| Sodium chloride | 900 mg |
| Water for injections | q.s.t. 100 mL |
| pH (adjusted with HCl or NaOH, if necessary) | pH between 4.5 to 8.5 |

(q.s.t = quantity sufficient to).

The formulation is prepared in order to contain 5,000 I.U. of sodium heparin per milliliter of solution in sterile presentation. The end product was bottled in flasks containing spray type applicator device (spraying pump), for administration of the product.

EXAMPLE 2

A pharmaceutical formulation was prepared in the form of a solution containing the following composition:

| SUBSTANCE | QUANTITY |
|---|---|
| Sodium heparin (~150 IU/mg) | 3,333.33 mg |
| Benzylalchool | 9.045 mL |
| Cremophor (surfactant) | 500.0 mg |
| Propyleneglycol | 10 mL |
| Sodium Chloride | 900 mg |
| Water for injections | q.s.t. 100 mL |
| pH (adjusted with HCl or NaOH, if necessary) | pH between 4.5 to 8.5 |

(q.s.t = quantity sufficient to).

This composition was prepared in order to present 5.000 I.U. of sodium heparin per milliliter of solution in sterile presentation. Presentation is made in flasks with a spraying pump (application pump) for local administration.

EXAMPLE 3

A pharmaceutical formulation was prepared in the form of a solution containing the following composition:

| SUBSTANCE | QUANTITY |
|---|---|
| Sodium heparin (~150 IU/mg) | 6,666.67 mg |
| Benzylalchool | 9.045 mL |
| Phosphate buffering 1.0 M | 1.5 mL |
| Sodium chloride | 330 mg |
| Water for injections | q.s.t. 100 mL |

(q.s.t = quantity sufficient to)

This composition was prepared in order to present 10.000 I.U. of heparin per milliliter of the solution in sterile presentation. It was packed in flasks with spray applicator device for topic administration.

Additionally, were prepared the compositions of the table hereunder, which have demonstrated great physical-chemical stability. All these compositions were prepared in pH between 4.5 and 8.5:

TABLE 1

| Example | Substance | Quantity |
|---|---|---|
| 4 | Heparin BPM[1] (~70 IU/mg) | 14,300 mg |
| | Benzylalchool | 9.045 mL |
| | Sodium chloride | 900 mg |
| | Water for injections | q.s.t. 100 mL |
| 5 | Heparin BPM[1] (~70 IU/mg) | 1,430 mg |
| | Methylparaben | 150 mg |
| | Propylparaben | 15 mg |
| | Sodium chloride | 900 mg |
| | Sorbitol | 5 g |
| | Water for injections | q.s.t. 100 mL |
| 6 Gel | Sodium heparin (~150 IU/mg) | 3,333.33 mg |
| | Benzylalchool | 9.045 mL |
| | Sodium chloride | 200 mg |
| | Propyleneglycol | 5 mL |
| | Steareth (surfactant) | 5,000 mg |
| | Carbomer | 2,000 mg |
| | Water for injections | q.s.t. 100 mL |
| 7 Gel | Sodium heparin (~150 IU/mg) | 666.67 mg |
| | Methylparaben | 150 mg |
| | Propylparaben | 15 mg |
| | Sodium chloride | 450 mg |
| | Glycerin | 5,000 mg |
| | Carbomer | 2,000 mg |
| | Water for injections | q.s.t. 100 mL |
| 8 | Heparin BPM[1] (~70 IU/mg) | 7,150 mg |
| | Benzetonium chloride | 0.020 mg |
| | Sodium chloride | 450 mg |
| | Citrate buffer | |
| | Water for injections | q.s.t. 100 mL |
| 9 Gel | Sodium heparin (~150 IU/mg) | 3,333.33 mg |
| | Benzylalchool | 9.045 mL |
| | Sodium chloride | 450 mg |
| | Propyleneglycol | 1,500 mg |
| | Steareth (surfactant) | 15,000 mg |
| | Methylcellulose | 4,350 mg |
| | Phosphate buffer (0.1 M) | 10 mL |
| | Water for injections | q.s.t. 100 mL |
| 10 | Heparin sulfate (~70 IU/mg) | 1,430 mg |
| | Ethanol | 100 mg |
| | Benzylalchool | 9.045 mL |
| | Sodium chloride | 450 mg |
| | Poloxamer | 300 mg |
| | Water for injections | q.s.t. 100 mL |

[1]Low molecular weight heparin;

Case 1

SAG—30 years, female, was burned by flame when handling alcohol, having 15% of corporeal area burned under $2^{nd}$ and $3^{rd}$ degrees, reaching face, cervical, thorax, and superior member. Started treatment with topic heparin composition one hour after the trauma. The composition was sprayed on injuries through the spraying device in a dose of approximately 5,000 IU per 1% of corporeal surface area affected, completing a total dose of 75,000 IU topically applied. Did not receive any opioid or another analgesic, not in entering or in the days following the treatment. Pain relief was observed few minutes after administration of the composition followed by injuries bleaching. The face edema was quite reduced when compared with that developed in similar cases. Treatment was continued with topic application twice a day, in a proportion of 5,000 IU for each 1% of burned area. In the following days the injuries became dry, with a fine protecting scab, with no pain for the patient, for which bathing applied in conventional treatments were interrupted. In the ninth day scabs began to naturally loosen, showing a new epithelium recently formed. This process was extended up to the $14^{th}$ day. Remained a small burned area of $3^{rd}$ degree that was grafted. The patient was released with sixteen days internment.

Case 2

E.A.S.—4 years, male was burned by scalding reaching the face, cervical region, thorax and shoulders totaling a corporeal surface area of 19.1%, involving $2^{nd}$ and $3^{rd}$ degrees. Treatment was initiated 1.5 hours after trauma, with the topic use of 20 mL of heparin composition in a concentration of 5,000 IU/mL, sprayed on the injuries twice a day, through the spraying device. Bleaching of the affected tissues was observed few minutes after administration. On the first day, was observed a small face edema and absence of pain, despite the non-utilization of conventional analgesic medication (opioid). Bathing for curatives were not necessary, since the injuries were dry and with a fine membrane that later on was transformed into a dry scab. On the fifth evolution day, the edges of the scab began to loosen showing the cicatrized underneath. Third degree areas were grafted on the eighth-day. On the fifteenth day the patient was released from hospital.

Case 3

L.C.F.—46 years, male, suffered burn by flame, involving 9% of corporeal surface, in 2nd degree burns. Treatment with heparin was started 13.5 hours after with topic administration of 10 mL (5,000 IU/mL) of the composition twice a day on the injuries. The edema established upon the beginning of the patient treatment, was considerably reduced some hours after the beginning of the treatment. During the treatment the patient did not present pain picture, the use of analgesic drugs was not necessary. Evaluation of the recovery picture presented during the treatment showed the non-necessity of making surgical curatives. On the fourteenth day, the injuries showed to be cicatrized, and the patient was released.

The invention claimed is:

1. A flask with a spray device enclosing a sterile topical pharmaceutical composition for treating skin or mucous injuries caused by burns, wherein such composition is an aqueous solution consisting of:

heparin or a pharmaceutically acceptable salt thereof, in an amount to provide from 5,000 to 10,000 International Units of heparin per milliliter of the final composition;

sodium chloride, in an amount ranging from 0.01 to 0.9% by weight based on the weight of the final composition;

benzyl alcohol, in an amount ranging from 0.0001 to 0.9% by weight based on the weight of the final composition;

polyoxyethylene derivatives of castor oil, in an amount ranging from 0.0001% to 0.5% by weight of the final composition;

water to complete 100% in weight of the final composition, and optionally hydrochloride acid or sodium hydroxide to adjust the pH between 4.5 and 8.5.

2. The flask with a spray device comprising a composition defined in claim 1, wherein the composition is sprayed on injuries through the spraying device in a dosage ranging form 1,000 to 50,000 International Units for each 1% of affected body surface area.

* * * * *